United States Patent [19]
Ashby

[11] Patent Number: 5,522,824
[45] Date of Patent: Jun. 4, 1996

[54] VALVULOTOME AND METHOD FOR MAKING AND USING SAME

[75] Inventor: Mark P. Ashby, Laguna Niguel, Calif.

[73] Assignee: Applied Medical Resources Corporation, Laguna Hills, Calif.

[21] Appl. No.: 185,555

[22] Filed: Jan. 24, 1994

[51] Int. Cl.$^6$ .................................................. A61B 17/32
[52] U.S. Cl. ........................................................ 606/159
[58] Field of Search ........................... 606/159, 170–171, 606/180, 15; 604/22

[56] References Cited

U.S. PATENT DOCUMENTS

| | | |
|---|---|---|
| 2,655,154 | 10/1953 | Richter . |
| 3,837,345 | 9/1974 | Matar . |
| 4,315,511 | 2/1982 | Chin ........................................ 606/159 |
| 4,449,321 | 1/1985 | Leather .................................. 606/159 |
| 4,493,321 | 1/1985 | Leather . |
| 4,528,982 | 7/1985 | Wellenstam ............................ 606/159 |
| 4,655,217 | 4/1987 | Reed . |
| 4,739,760 | 4/1988 | Chin et al. . |
| 4,768,508 | 9/1988 | Chin et al. . |
| 4,791,913 | 12/1988 | Maloney . |
| 4,924,882 | 5/1990 | Donovan . |
| 4,952,215 | 8/1990 | Ouriel et al. . |
| 5,026,383 | 6/1991 | Nobels et al. . |
| 5,047,041 | 9/1991 | Samuels . |
| 5,049,154 | 9/1991 | Quadri .................................... 606/159 |
| 5,061,240 | 10/1991 | Cherian ............................. 606/159 X |
| 5,069,679 | 12/1991 | Taheri .................................... 606/159 |
| 5,092,872 | 3/1992 | Segalowitz ............................ 606/159 |
| 5,133,725 | 7/1992 | Quadri .................................... 606/159 |
| 5,141,491 | 8/1992 | Bowald ............................. 606/159 X |
| 5,152,771 | 10/1992 | Sabbaghian et al. ................. 606/159 |
| 5,171,316 | 12/1992 | Mehigan ................................ 606/159 |
| 5,284,478 | 2/1994 | Nobles et al. ......................... 606/159 |
| 5,370,651 | 12/1994 | Summers ............................... 606/159 |

FOREIGN PATENT DOCUMENTS

| | | | |
|---|---|---|---|
| 527312 | 2/1993 | European Pat. Off. ................ | 606/159 |
| 3717926 | 5/1987 | Germany ......................... | A61B 17/32 |
| 8909029 | 10/1989 | WIPO ..................................... | 606/159 |

OTHER PUBLICATIONS

"Leather Retrograde Valvulotome", Baxter Healthcare Corporation brochure, Chicago, Illinois, 1988, pp. 1–2.
"Angioscopic Valvulotome", Intramed, San Diego, California, 1992, pp. 1–4.
Scanlan International Surgical Instrumentation Catalog, Scanlan International, Inc., St. Paul, MN, 1988, pp. 53–54.
"Leather Karmody In Situ Bypass Set", American V. Mueller division of Baxter Healthcare Corp., Chicago, IL, 1988, pp. 124, 125.
"Instructions, Valvulotome (Detachable Type)" Olympus Optical, Tokyo, Japan pp. 1–3.

*Primary Examiner*—Stephen C. Pellegrino
*Assistant Examiner*—Nancy Mulcare
*Attorney, Agent, or Firm*—Richard L. Myers

[57] ABSTRACT

A valvulotome for disrupting a valve in a vein includes an elongate control member and a cutting head disposed at the distal end of the control member. The cutting head includes an elongate section extending generally along the length of the cutting head and a return section extending beside the elongate section also along the length of the cutting head. A cutting section included in the cutting head extends between the elongate section and the return section at a particular angle to the length of the control member. Portions of this cutting section form a proximally facing cutting edge for disrupting the valve. The valvulotome can be used with an endoscope in a method wherein the cutting head is tied to the endoscope with a suture, or a method wherein the valvulotome is back-loaded into the working channel of the endoscope.

27 Claims, 5 Drawing Sheets

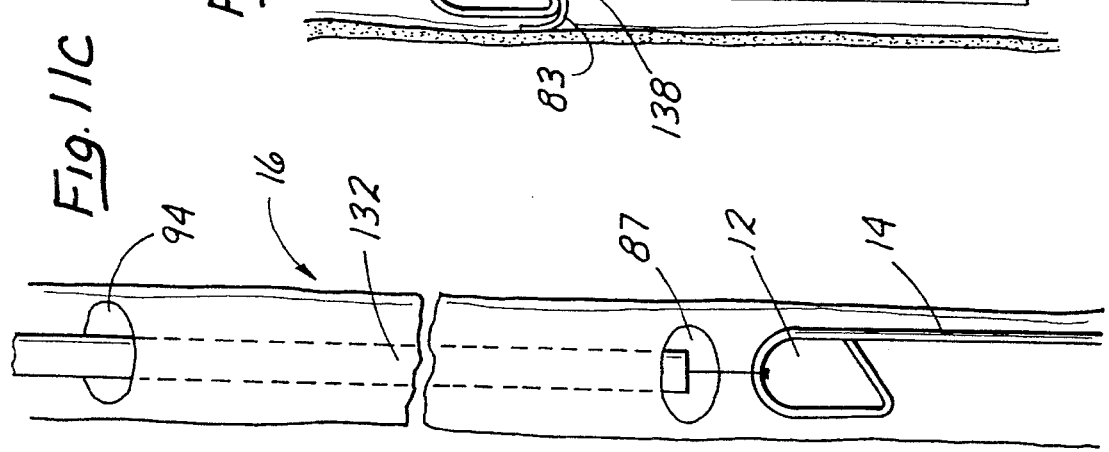
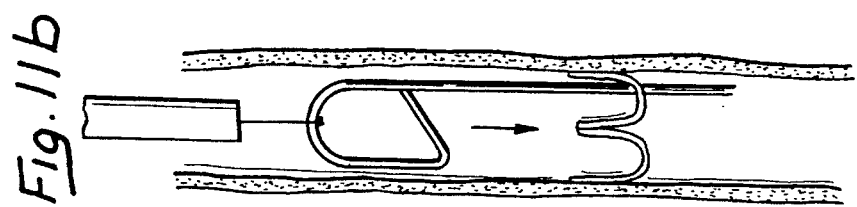
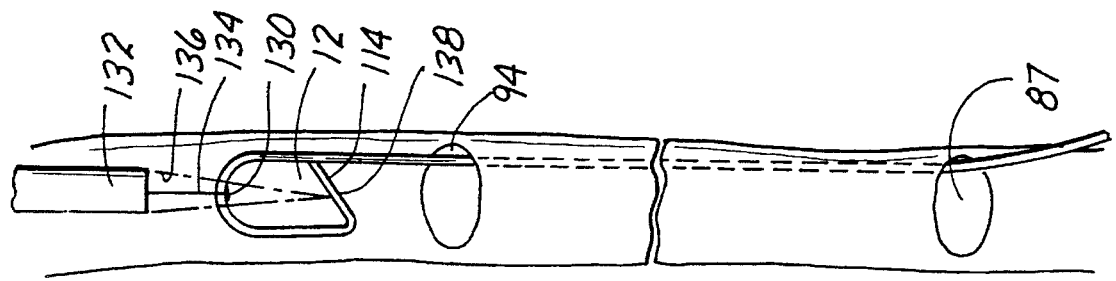
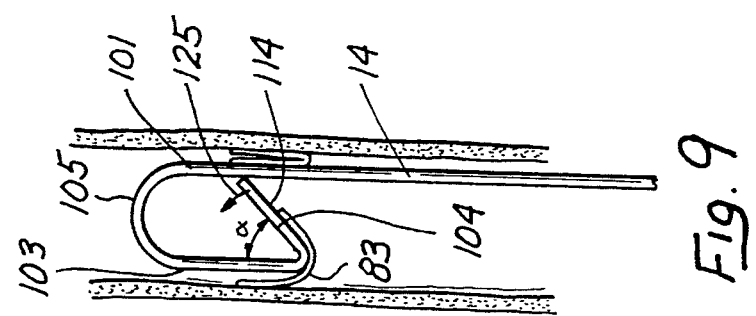

VALVULOTOME AND METHOD FOR MAKING AND USING SAME

BACKGROUND OF THE INVENTION

1. Field of the Invention

This invention relates generally to the apparatus and method for disrupting vein valves in a mammal.

2. Discussion of the Prior Art

It is well known that the vascular system is relied on to nourish the cells of the body and to remove waste materials from the cells of the body. More specifically, the arteries of the vascular system convey oxygen and other nutrients to the cells, while the veins of the vascular system return the blood and waste materials from the cells to the lungs, liver, heart and other organs of the body. Since the flow of blood from the extremities is generally upward, this return flow of blood in the veins must work against the force of gravity. To assist with the return flow, veins commonly include several valves which permit a flow of blood in the upward direction while inhibiting a flow of blood in the downward direction. Thus, the vein valves in their normal state aid in moving the blood in an upward direction from the extremity to the organs of the body.

The circulation of blood to and from the cells presents the greatest problem in the extremities of the body, such as the hands and feet, where the cells are located the greatest distance from the organs.

When blood is not appropriately circulated, the unnourished cells die. This can result in loss of the associated hand or foot.

In order to avoid amputation, it has long been known that circulation to these extremities must be enhanced particularly in old age. When for example, the femoral artery becomes blocked, it is advantageous to bypass this blockage in order to enhance the flow of blood to the lower leg and foot. In a common procedure, the saphenous vein is used for this purpose. Particularly when the blockage occurs in the upper region of the femoral artery, the saphenous vein can be harvested and reversed before attachment to the femoral artery above and below the blockage. This reversal of the vein orients the valves in a direction which facilitates a flow of blood toward rather than away from the extremities. This procedure for reversing the vein does not work as well in the lower regions of the femoral artery where the distal and proximal diameters of the artery and vein become incompatible.

Particularly for these lower regions, an in-situ procedure has evolved where the saphenous vein is left in place but its valves are disrupted in order to enhance a flow of blood in the reverse direction, toward rather than away from the extremity. In this procedure, the proximal end of the vein is attached to the proximal end of the artery, while the distal end of the vein is attached to the distal end of the artery. These similar ends are more compatible in size. When the valves are disrupted, the flow of blood in a reversed direction through the vein is enhanced to promote circulation to the extremity. Although conversion of the saphenous vein to an arterial function reduces the amount of venous conduit for return blood flow, it has been found that the remaining veins will typically be sufficient to accommodate the requirements of return blood flow.

This disruption of the valves is accomplished with an instrument referred to as a valvulotome. Although various valvulotomes have been used, they sometimes fail to adequately cut the valve in order to lower the resistance to downward blood flow.

One common variety of valvulotome is disclosed by Mehigan in U.S. Pat. No. 5,171,316. This instrument has a triangular head which offers no resistance to the undesirable engagement of sidebranches of the vein. The cutting edge is disposed at a 90° angle to the axis of the vein and for this reason tends to cut a valve cusp from the inside out. This typically results in reduced cutting so that the valve cusp continues to form a cup thereby inhibiting blood flow in the reverse direction. In another valvulotome disclosed by Nobles in U.S. Pat. No. 5,026,383, a cutting tip including two prongs is used to engage two valve cusps from the downstream side of the valve. This instrument has had limited success since the cut of the cusps is typically limited to one-half the distance separating the prongs. Nevertheless, Nobles discloses that a scope can be positioned to view the cutting operation from the proximal side of the prongs, and a distal catheter can be connected between the prongs to facilitate movement of the valvulotome in the upstream direction.

SUMMARY OF THE INVENTION

The valvulotome of the present invention is easily manipulated with a control member to cut one cusp of the valve at a time. This valvulotome includes a cutting head which has a length extending along the axis of the vein and a width which is greater than the radius of the vein. It includes an elongate member which may comprise an extension of the control member and a return section which extends backwardly beside the elongate member. A lateral section connects the return section to the elongate section and forms the distal-most point of the cutting head. This lateral section is preferably free of sharp corners so that the valvulotome can be moved easily in a distal direction.

A cutting section is disposed at a particular angle to the return section. This angle is preferably less than 90°. In an embodiment where the elongate section and return section are parallel, this same angle separates the cutting section from the elongate section as well as the axis of the vein. A transition section disposed between the return section and the cutting section includes the proximal-most point of the cutting head.

In a preferred embodiment, the lateral section and the transition section each have a circular configuration and a radius, but the radius of the transition section is smaller than that of the lateral section. A cutting edge formed along the cutting section may also extend into the transition section. This brings the cutting edge into close proximity to the proximal-most point of the cutting head.

The particular angle is chosen so that the greatest pressures are exerted at the transition section. This promotes cutting of the cusp from the outside inwardly, and increases the length of the cut through the cusp.

This valvulotome is particularly adapted for use with an endoscope. The valvulotome can be inserted from a first incision below the valve to exit the vein at a second incision above the valve. When the valvulotome has cleared the second incision, an endoscope can be sutured to the valvulotome and the two instruments drawn back through the second incision to engage the valve. This endoscope typically has a focal point so that the endoscope can be fixed to the valvulotome at a distance which permits the focal point to be disposed along the cutting edge of the valvulotome. This enhances the focus at the critical point of cutting.

In a further embodiment, the endoscope can be inserted through the first incision with the valvulotome attached to its distal end. This configuration promotes cutting of the valve from above the valve while viewing the cutting operation from below the valve.

In one aspect, the invention includes a valvulotome for disrupting a valve in a vein extending upstream from a heart to an extremity of the body. The vein is further characterized by a radius and a central axis. The valvulotome includes an elongate control member having a distal end and a length sufficient to position the distal end downstream of the valve from an entry site upstream of the valve. A cutting head having a length and a width is coupled to the distal end of the control member. This cutting head includes an elongate section extending along the length of the cutting head, and a return section extending beside the elongate section generally along the length of the cutting head. The cutting head includes a cutting section which it extends between the elongate section and the return section at a particular angle to the length of the control member. Portions of this cutting section are sharpened to form a proximal facing cutting edge for engaging and cutting the valve to disrupt the valve of the vein.

In another aspect of the invention, a transition section extends between the return section and the cutting section at the proximal end of the cutting head. Portions of at least one of the transition section and the cutting section define the proximally facing cutting edge of the valvulotome.

In an additional aspect of the invention, the valvulotome is combined with an endoscope which has a focal length and is sized and configured for insertion into the vein. This combination includes means for coupling the endoscope to the distal end of the cutting head at a particular distance dependent upon the focal length of the endoscope.

In still a further aspect of the invention, a method for disrupting a valve in a vein comprises the steps of providing an elongate valvulotome having a cutting head and an endoscope having a focal point. The cutting head of the valvulotome is inserted into the vein through a first incision and moved downstream through the valve exiting the vein through a second incision. At this point, the distal end of the endoscope is coupled to the distal end of the cutting head and the combination pulled back into the vein through the second incision. Further movement of the cutting head in the upstream direction disrupts the valves in the vein. During this cutting step, the valve can be viewed through the endoscope from a position downstream of the cutting head.

These and other features and advantages of the invention will become more apparent with a discussion of preferred embodiments and the best mode of the invention in combination with the associated drawings.

DESCRIPTION OF THE DRAWINGS

FIG. 9 is a side view of the valvulotome similar to FIG. 6 but with the cutting section pivotal to increase pressure in a transition region;

FIG. 11a illustrates a preferred method wherein the valvulotome is inserted through an entry site and moved through an exit site for coupling with an endoscope;

FIG. 11b illustrates a further step wherein the method wherein the valvulotome is drawn with the endoscope through the exit site and a vein valve;

FIG. 11c illustrates a further step in the method wherein the valvulotome is removed through the entry site and the endoscope disengaged for removal through the exit site;

FIG. 12 is a side view of a further combination including an endoscope and a valvulotome attached to the distal end of the endoscope a distance sufficient to focus the endoscope on a cutting edge of the valvulotome;

FIGS. 13A–15 illustrate steps in a preferred method for assembling the combination of an endoscope and a valvulotome of the present invention;

FIG. 13A illustrates a side elevation view of the valvulotome including a control member;

FIG. 15 illustrates a side view of the valvulotome-endoscope combination with a torque handle permanently fixed to the control member of the valvulotome.

DESCRIPTION OF PREFERRED EMBODIMENTS AND BEST MODE OF THE INVENTION

Figures 1, 3:
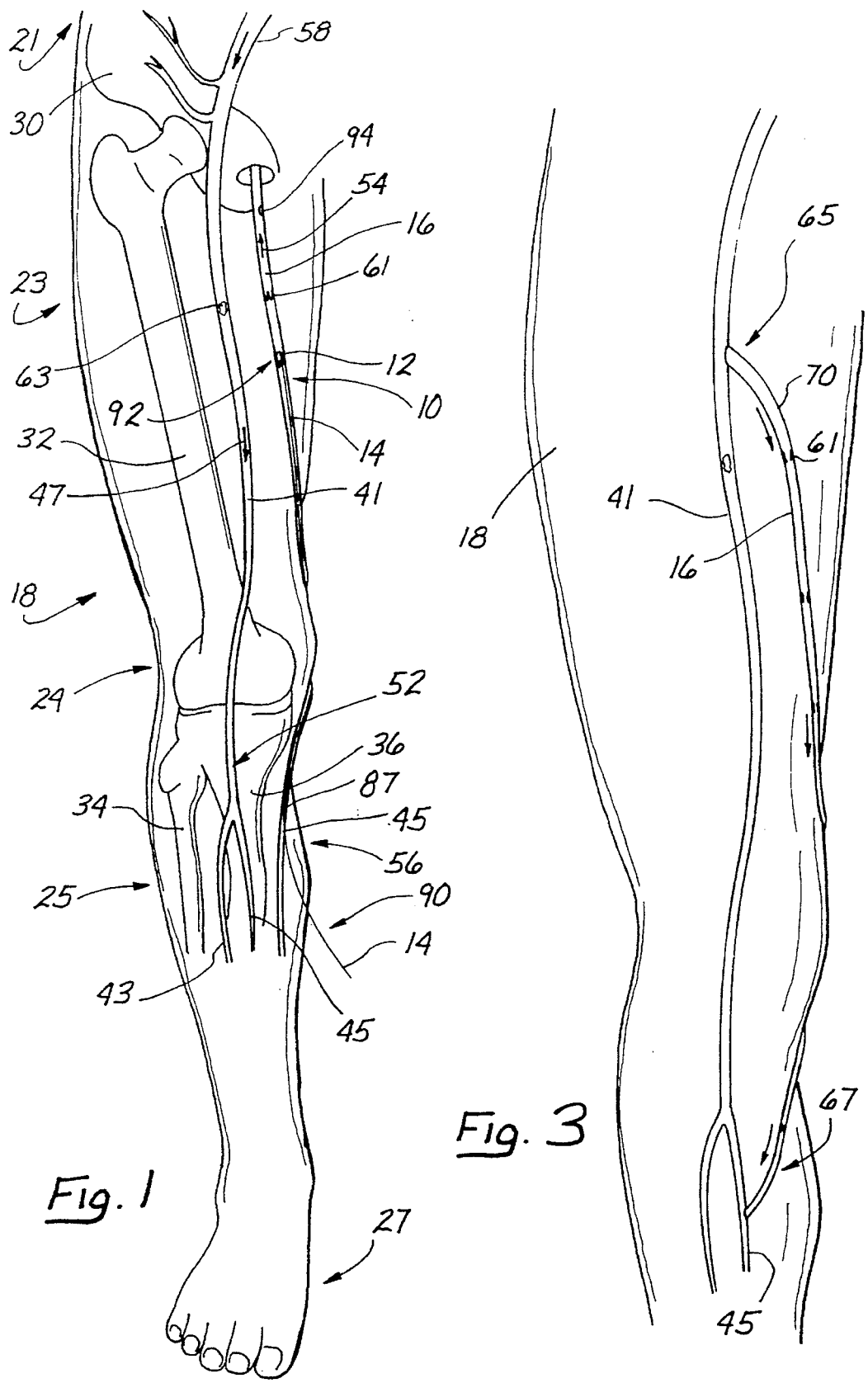
FIG. 1 is a front perspective view of a human leg including an artery with a blockage and a saphenous vein with vein valves.
FIG. 3 is a perspective view of the leg with the saphenous vein retained insitu and the valves disrupted to bypass the blockage in the artery.

A valvulotome is illustrated in FIG. 1 and designated generally by the reference numeral 10. The valvulotome 10 includes a cutting head 12 and a control member 14.

Figure 6:
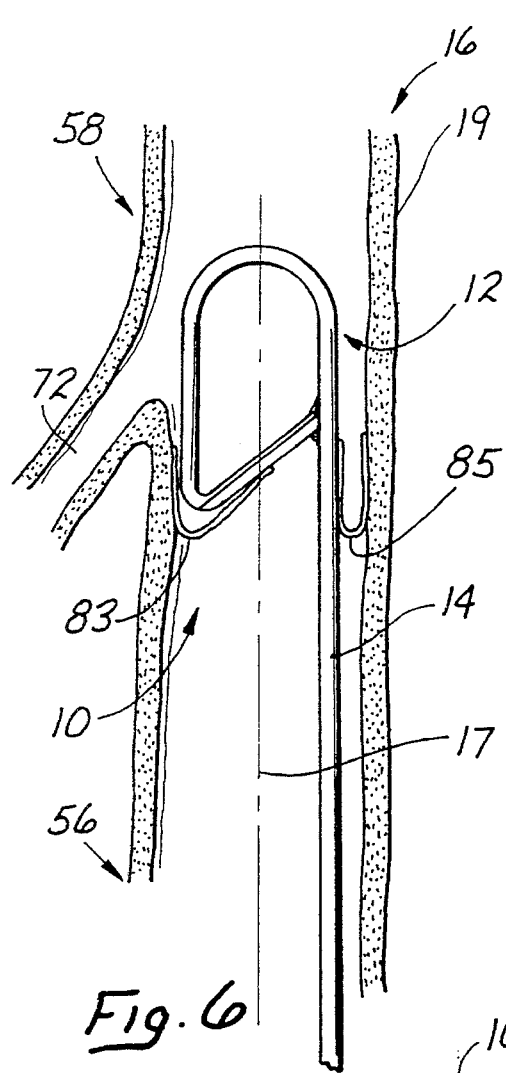
FIG. 6 is a side view of one embodiment of the valvulotome of the present invention.

In FIG. 1 the valvulotome 10 is illustrated to be operatively disposed in the saphenous vein 16 of a leg 18. the vein 16 has a central axis 17 and a vessel wall 19 which are best illustrated in the enlarged view of FIG. 6. As described in greater detail below, it is the purpose of the valvulotome 10 to prepare the saphenous vein 16 for use as a bypass graft in order to increase the flow of blood to an extremity of the human body. Although the leg 18 is illustrated in FIG. 1, it will be apparent that the valvulotome 10 can be equally effective in preparing other veins such as those occurring in the arms (not shown) to improve circulation for example to the hand.

The leg 18 extends downward from a groin 21 and includes an upper leg or thigh 23, a knee 24, and a lower leg 25 which is connected to a foot 27. The skeletal structure in this region includes a pelvis 30, a femur 32, in the thigh 23, and a tibia 34 and fibula 36 in the lower leg 25.

In the extremities, the circulation system is of greatest interest to the present invention. This system includes arteries which carry blood from the heart (not shown) to the distal regions of the body. In the leg 18, the primary artery is the femoral artery 41 which extends from the area of the groin 21 past the knee 24 into tributaries including the peroneal artery 43 and the posterior tibial artery 45. It follows that in the femoral artery 41, downstream is toward the extremity, such as the foot 27, and upstream is toward the groin 21. It is the blood flowing in the femoral artery 41 which carries oxygen and other nutrients to the foot 27.

The circulatory system also includes the venous system which carries blood with carbon dioxide and various waste products from the cells at the extremities back to the organs, such as the heart (not shown). In the abdomen, the kidneys remove the waste products from the blood, the lungs oxygenate the blood, and the heart pumps the nutrified blood back into the femoral artery 41.

In the femoral artery 41, blood flows in the direction of an arrow 47 from an upstream end 50 of the groin 21 to a downstream end 52 in the lower leg 25. In the vein 16, the flow is reversed. This flow is in the direction of an arrow 54 from an upstream end 56 to a downstream end 58.

When a person is standing, blood flow in the femoral artery 41 is enhanced by gravitation. However, blood flow in the vein 16 is resisted by gravity. For this reason, the vein 16 commonly includes several valves 61 which facilitate flow toward the downstream end 58 but which inhibit flow toward the upstream end 56. With these valves 61, the flow of blood in the saphenous vein 16 is encouraged against the gravitational force.

The problem being solved by the present invention occurs when the flow of blood to the extremities, such as the hand or foot 27, is insufficient to nourish the cell in those distal regions. This reduced blood flow may result from blockage such as an embolus 63, or arterial sclerosis, a thickening of the vessel walls. In order to improve this blood flow, it is desirable to bypass any restricted portion of the femoral artery with a graft which can carry the nutritive blood parallel with the damaged artery 41. The saphenous vein 16 has been used for this purpose. Turning this vein into an arterial graft removes it from the venous system but other veins can pick up the additional demand for return blood flow.

As previously noted, the vein 16 is not merely a conduit which can easily accommodate flow in either direction. The presence of the valves 61 greatly impedes any attempt to accommodate blood flow from the groin 51 to the lower leg 25. In some cases such as that illustrated in FIG. 2, the vein 16 has been harvested from the leg 18 and actually turned around prior to attachment at a proximal site 65 upstream of the blockage or embolus 63 and a distal site 67 downstream of the blockage or embolus 63.

Figure 2:
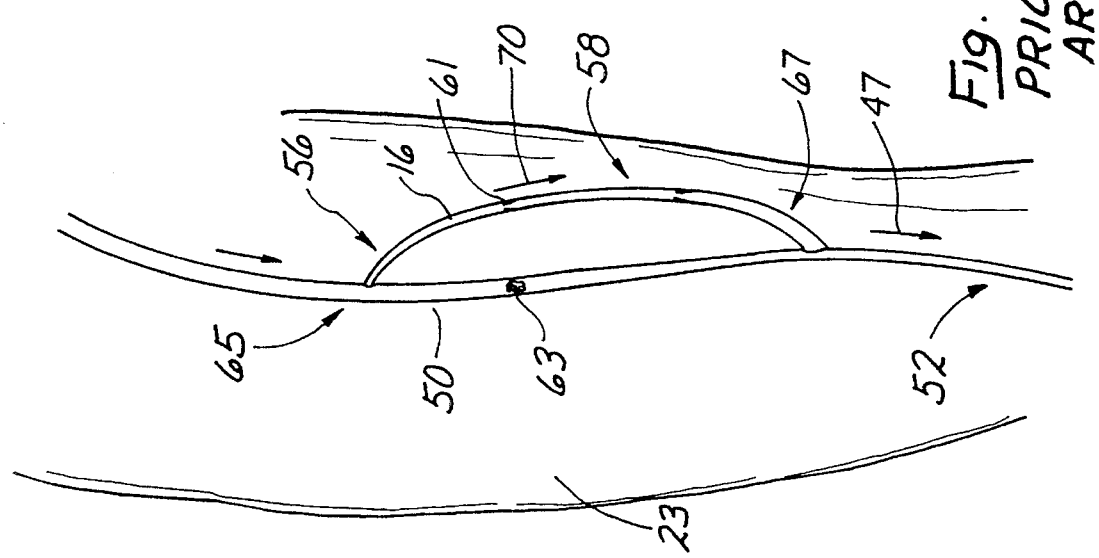
FIG. 2 is a perspective view of the upper leg with the saphenous vein reversed for bypassing the blockage in the artery.

This procedure for reversing the vein 16 works best in the thigh 23 where the artery 41 and vein 16 maintain a fairly constant diameter. But the procedure is much less effective for bypassing greater lengths of the artery 41 due to the reduced diameters of both the artery 41 and vein 16 in the regions of the lower leg 25. In FIG. 2, these diameters are exaggerated where the narrow upstream end of the vein 16 is connected to the enlarged upstream end of the artery 41 at the site 65. This mismatch also occurs at the distal site 67 where the vein 16 is enlarged but the artery 41 is reduced in diameter. Nevertheless, this procedure for reversing the vein 16 orients the valves 61 in a manner that flow toward the extremity, such as the foot 27, is facilitated rather than inhibited. Reversing the vein 16, also reverses the valve 61 so the flow is now accommodated in the downward direction as shown by the arrow 70.

In order to provide a greater length of bypass graft, it has been necessary to leave the saphenous vein in its normal orientation, but to disrupt the valve 61 so the downward flow in the direction of arrow 70 can be accommodated. This alternative procedure, which is illustrated in FIG. 3, is of greatest interest to the present invention. In this case, the proximal site 65 may be in the region of the groin 21, while the distal site 67 might be in the lower leg 25 where the vein 16 is connected to the artery 45.

Various prior art valvulotomes have been used to disrupt the valves in the saphenous vein 16. In some cases, various blunt instruments have been used to tear the leaflets of the valve, it being felt that any disruption would be tolerable to accommodate reversed blood flow. Other instruments have been provided with sharpened surfaces to more precisely cut the leaflets of the valve. Two of these prior art instruments are illustrated in FIGS. 4 and 5.

Figure 4:
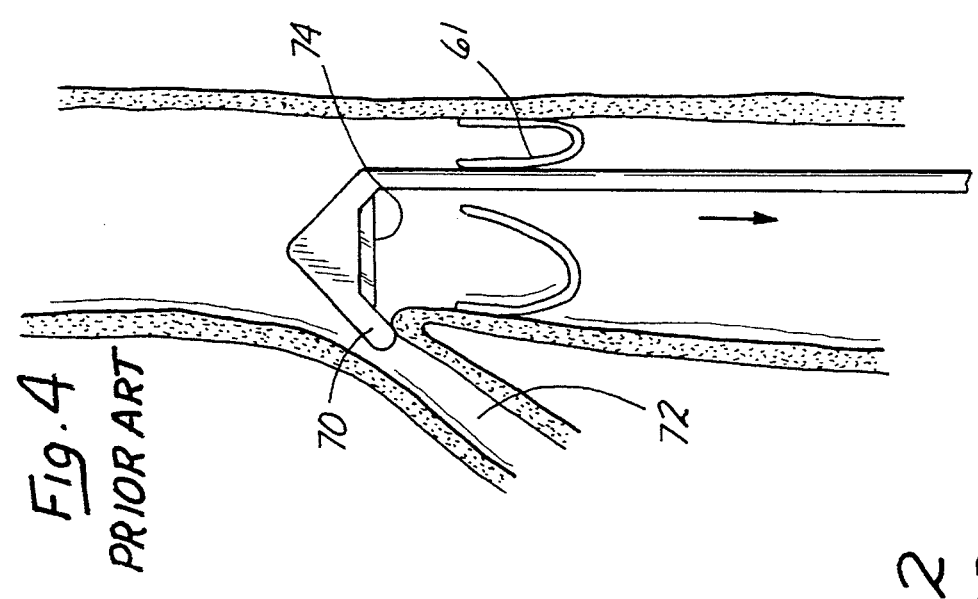
FIG. 4 is a side view of a prior art valvulotome disposed in a vein.

The device of FIG. 4 was previously mentioned with reference to its U.S. Pat. No. 5,171,316. This device is not particularly elongate and has been provided with a blunt lateral nose 70. While this blunt nose 70 has generally protected the walls of the vein 16 from being cut, it has tended to extend into tributary veins, such as the vein 72, exposing the vein junction to a sharpened edge 74. Under these circumstances, this valvulotome of the prior art has greatly damaged the wall of the vein 16.

Figure 5:
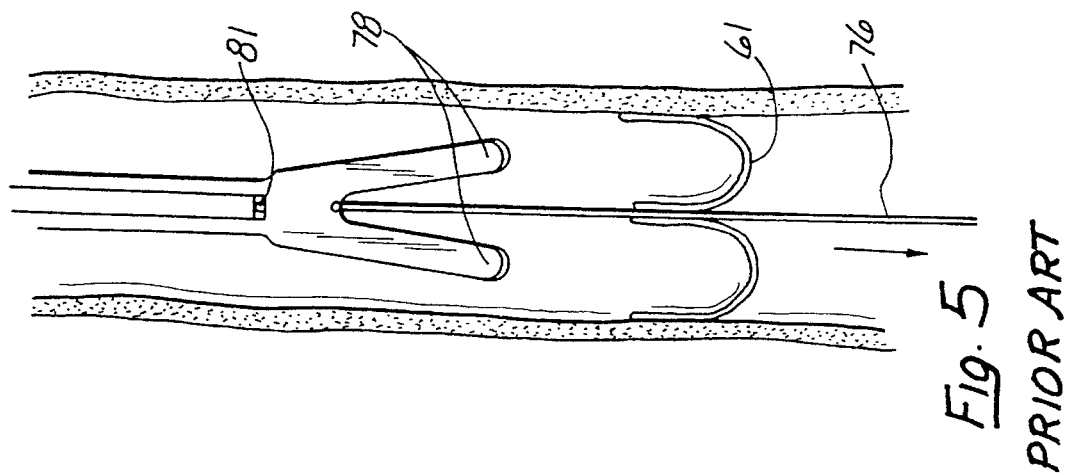
FIG. 5 is a side view of another valvulotome disposed in a vein.

The prior art valvulotome illustrated in FIG. 5 is pulled through the vein 16 in the upstream direction by a pulling catheter 76 which is attached to cutting prongs 78. Two of these prongs 78 are provided in an attempt to cut or disrupt multiple valve leaflets at the same time. The prongs 78 have been maintained in a fixed space relationship so that the cutting characteristics of the larger valves 61 have differed considerably from those associated with the smaller valves 61. It follows that the disruption of the valves has been unrepeatable and unpredictable. An endoscope 81 has been used with this valvulotome to facilitate viewing of the cutting operation The valvulotome 10 of the present invention greatly improves the ability to cut the leaflets of the vein 61 while reducing any possibility for damage to the primary vein 16 or tributary veins 72. Referring briefly to FIG. 1, it can be seen that in a typical operating procedure, the cutting head 12 can be inserted through a lower incision 87 into the vein 16 and through the valve 61. Pulling a proximal end 90 of the control member 14 (which has been left extending through the incision 87) draws the cutting head 12 at a distal end 92 of the control member 14 proximally back through the vein 16. In this procedure, the cutting head 12 disrupts each of the valves 61 thereby facilitating blood flow in the reverse direction. An upper incision 94 may also be provided in another procedure described in greater detail below.

In FIG. 6 the vein 16 is illustrated to have the central axis 17. In order to inhibit any tendency for the cutting head 12 to engage tributary veins (such as the vein 72) as it moves through the primary vein 16, it is desirable to maintain a generally parallel orientation between the cutting head 12 and the axis 17. This desired orientation is facilitated by providing the cutting head 12 with a length which is sufficiently long to keep the cutting head 12 from pivoting within the vein 16. The length of the cutting head 12 may be several times the width of the cutting head 12 which is preferably greater than the radius of the vein 16. These relative dimensions are illustrated in the enlarged view of FIG. 6 where the valve 61 is shown to include two cusps 83 and 85.

In this embodiment, the cutting head 12 has an elongate section 101, a return section 103, and a lateral section 105 disposed therebetween at the distal end 90 of the valvulotome 10 and cutting head 12. The cutting head 12 also includes a cutting section 107 which extends between the return section 103 and the elongate section 101. A transition section 109 connects the cutting section 107 to the return section 103 (at an angle α), and includes the proximal-most point 112 of the cutting head 12. The cutting section 107 is sharpened to form a cutting edge 114 along a major portion of the width of the cutting head 12 defined by the separation of the width of the cutting head 12. In the illustrated embodiment, this width is defined by the distance separating the elongate section 101 and the return section 103.

A preferred embodiment of the valvulotome 10 can be formed from a single wire having a circular cross section. The wire will typically be formed of stainless steel and may have a diameter such as 0.14 inches. To produce the cutting head 12, the elongate section 101 can be formed as an extension of the control member 14. The wire can the be bent back on itself through the lateral region 105 preferably along an arc which may be a circle having a radius R such as 0.035 inches. In this embodiment, the diameter of the circle forming the lateral region 105 generally defines the width of the cutting head 12. After the wire is bent back on itself through the lateral region 105, the return section 103 extends backwardly along and generally parallel to the elongate section 101.

At the proximal end of the return section 103, the wire can again be bent back on itself through the angle α. The radius r of this bend is smaller than the radius R at the lateral section 105, and may be for example 0.010 inches. If the elongate section 101 and the return section 103 are parallel, this angle α also exists between the cutting region 107 and the elongate section 101. When operatively disposed within the vein 16, the angle α will also exist between the cutting edge 114 and the axis 17 of the vein 16.

In this embodiment, the cutting section 107 is straight although this is not required by the invention. In other embodiments, the cutting section 107 may bend increasingly toward the elongate section 101 or bend increasingly away from the elongate section 101. The end of the wire forming the cutting section 107 can be left free of the elongate section 101 or attached to the elongate section 101 for example by a weld 115.

Figure 8A:
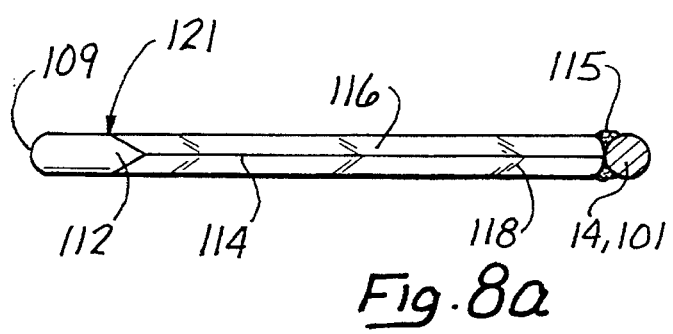
FIG. 8a is a cross section view taken along lines 8a—8a of FIG. 7.
Figure 8:
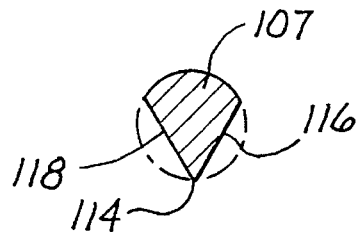
FIG. 8 is a cross section view taken along lines 8—8 of FIG. 7.

The cutting edge 114 is best illustrated in the cross-sectional view of FIG. 8. From this view it can be seen that the circular wire forming the cutting head 12 can be ground to form lateral surfaces 116, 118 which extend to the cutting edge 114.

The orientation of this cutting edge 114 in the cutting section 107 and transition section 109 is of particular interest to the present invention. It is generally desirable that the outermost surface of the cutting head 12 have no sharpened edges or projections. Thus the rounded surface of the wire forming the elongate section 101, the lateral section 105, and the return section 103 is preferred. It is also desirable that these rounded characteristics extend along at least a portion of the transition section 109. In the illustrated embodiment, these rounded characteristics are insured by stopping the cutting edge 114 short of the proximal-most point 112. This is perhaps best illustrated in FIG. 8a where the proximal-most point 112 is shown to be within a wedge 121 formed between the lateral surfaces 116 and 118.

Disruption of the valve 81 is enhanced when the angle α is such that the cutting section 107 can enter the cusp 83 and initially exert a pressure on the cusp 83 which is greater in proximity to the return section 103 than in proximity to the elongate section 101. If the angle α were 90°, as in the prior art, this characteristic would not occur. Due to the natural formation of the cusp 83, an angle α of 90° unfortunately produces the greatest pressure in proximity to the elongate section 101. As a consequence, cutting with this prior art configuration starts at the inner edge of the cusp 83 and progresses outwardly. By providing the cutting head 12 with an angle α which is less than 90°, pressure is increased in the transition region 109 so that cutting tends to occur along the cusp 83, from the outside of the cusp 83 inwardly. This tends to increase the length of the cusp thereby providing for a greater disruption of the valve 61. In one preferred embodiment, including the weld 115, the angle α is fixed in a range between 55° and 61°. In this range, cutting of the valve cusp 83 begins in proximity to the wall of the vein 16, and progresses inwardly to the central edge of the cusp 83.

In another preferred embodiment illustrated in FIG. 9, the cutting section 107 is not welded to the elongate section 101 so that the cutting edge 114 is free to pivot along an arrow 125 toward the return section 103 progressively decreasing the angle α. With this freedom of movement, the angle α is progressively decreased thereby progressively increasing the pressure at the transition region 109 until cutting occurs at the proximal-most point 112.

Figure 7:
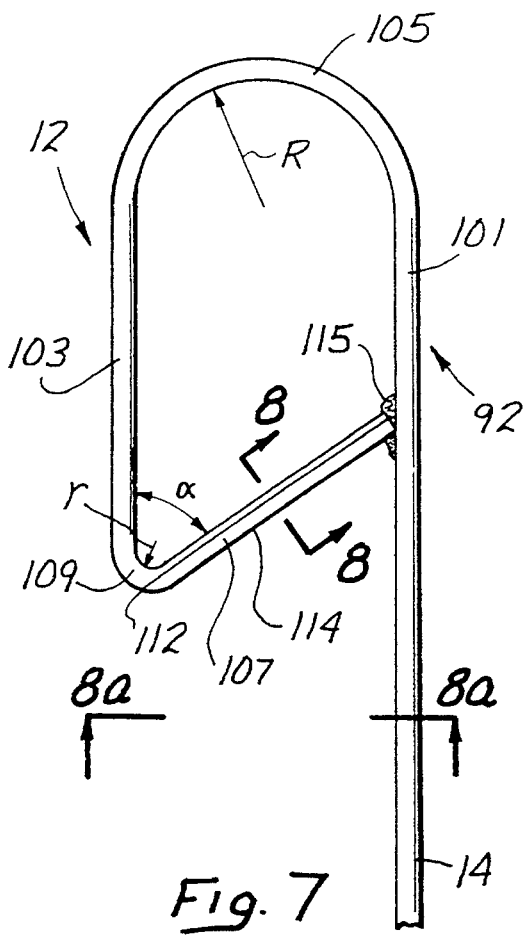
FIG. 7 is an enlarged side view of a cutting head associated with the valvulotome of FIG. 6.
Figure 10:
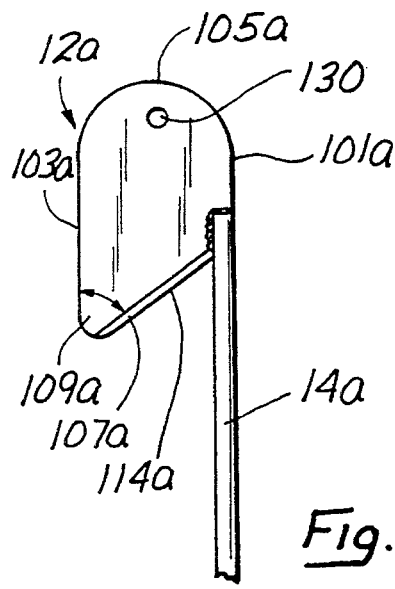
FIG. 10 is an additional embodiment of the valvulotome of the present invention including a cutting head having a blade configuration.

The invention can also be embodied as illustrated in FIG. 10 wherein similar structural elements are designated by the same reference numeral, followed by the lower case "a". Thus the embodiment of FIG. 10 includes a control member 14a and cutting head 12a. In this case however, the cutting head 12a is formed in a blade configuration but has lateral surfaces 101a, 103a, 105a, 107a and 109a which are similar to the sections 101–109 previously described. Thus the surfaces 101a, 103a and 105a are preferably free of sharp edges and projections. Also, the surfaces 101a and 103a have a generally parallel disposition which tends to maintain the alignment of these surfaces as well as the cutting head 12a generally parallel to the axis 17 of the vein 16. The cutting surface 107a is disposed at the angle α to the surface 103a but preferably extends outwardly from the surface 101a a distance which is short of the surface 103a. This insures that cutting does not occur too close to the wall of the vein 16. In this embodiment, the blade forming the cutting head 12a can be welded or otherwise attached to the control member 14a. A hole 130 can be provided near the distal end of the cutting head 12a to facilitate visualization as discussed in greater detail below. In the embodiment of FIG. 7, this hole 130 occurs naturally with the spacing of the wire which forms the elongate section 101 and return section 103.

In the past, valvulotomes have been inserted through the lower incision 87 and forced upwardly through the valves 61. Withdrawing the valvulotome 10 has tended to disrupt the valves 61 sufficiently to promote reversed flow. Early attempts at valve disruption were conducted blindly. More recently, endoscopes have been used to view the cutting of each valve. One such system has been discussed with reference to the prior art of FIG. 5.

The valvulotome 10 of the present invention is particularly adapted for use in a procedure which greatly improves visualization of the valve cutting. In this procedure, the cutting head 12 is introduced through the lower incision 87 upwardly through the valves 61 in a manner previously discussed. The upper incision 94 is formed above the last valve to be cut, and the cutting head 12 is passed outwardly through this incision as illustrated in FIG. 11a. With the cutting head 12 outside the vein 16, an endoscope 132 can be attached, for example by a suture 134, through the hole 130.

The endoscope 132 will commonly include fiberoptics which at the distal end of the endoscope focus light along a focal length 136 to a focal point 138. The length of the suture 134 in a preferred method is chosen so that the focal point 138 is disposed along the cutting edge 114 of the cutting head 112. Maintaining this distance ensures that images along the cutting edge 114 are maintained in relatively sharp focus.

After the suture 134 is attached to the endoscope 132 at the distal end 92 of the valvulotome 10, the assembled combination can be drawn back through the upper incision 94 downwardly into the vein 16. As the cutting head 12 approaches a valve 61, the sharp focus of the endoscope 132 along the cutting edge 114 gives a clear view of the operation prior to and during valve disruption. Sequentially and perhaps repeatedly disrupting the cusps 83 and 85 of the valves 61 will ultimately bring the cutting head 12 to the lower incision 87. At this point, the cutting head can be removed through the incision 87 and the suture 134 cut to permit separation of the valvulotome 10 and the endoscope 132. Thus separated the endoscope 132 can be drawn upwardly through the vein and removed through the upper incision 94.

In a further combination associated with the present invention the proximal end of the valvulotome 10 can be attached to the distal end of the endoscope 132. This attachment will typically be accomplished by inserting the control member 14 into the working channel (not shown) which is commonly provided in the endoscope 132. The control member 14 can be attached or otherwise fixed in this position, so that the focal point 138 of the endoscope 132 lies along the cutting edge 114 to achieve the advantages previously discussed. It will be noted that in this embodiment of the invention, the cutting edge 114 faces toward the endoscope 132. This offers the unique combination of advantages which facilitates viewing of the valve disruption with only a single lower incision 87. Both the cutting head 12 and the endoscope 132 in this assembly can be inserted through the lower incision 87 with at least the cutting head 12 extending through the most distal of the valves to be disrupted. Drawing this assembly downwardly enables the cusps 83, 85 to be cut. Notably, this cutting can be viewed from the opposite side of the valve 61.

Figure 13A:
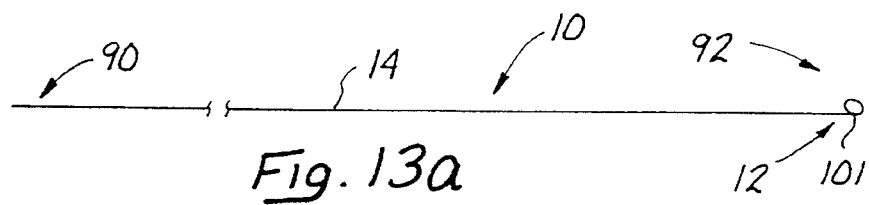
Figure 13B:
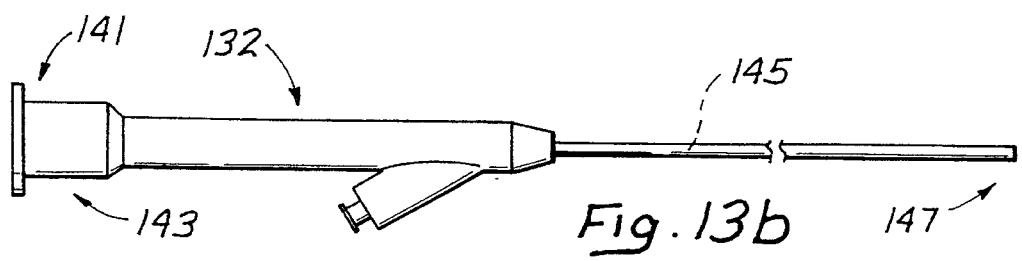
FIG. 13B illustrates a side elevation view of an endoscope having a working channel.
Figure 14A:
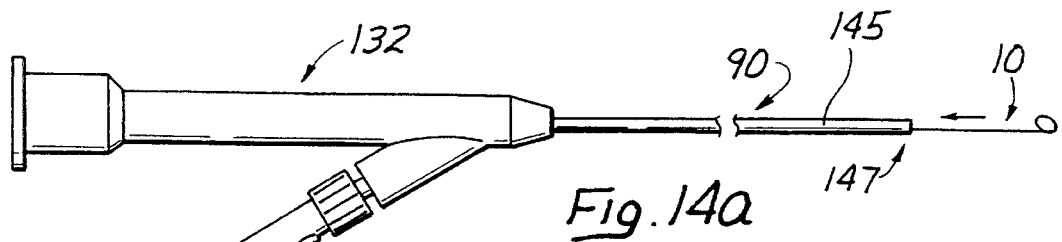
FIG. 14A illustrates an assembly step whereby the control member of the valvulotome is back-loaded into the working channel of the endoscope; and a pin vice is attached to the valvulotome.
Figure 14B:
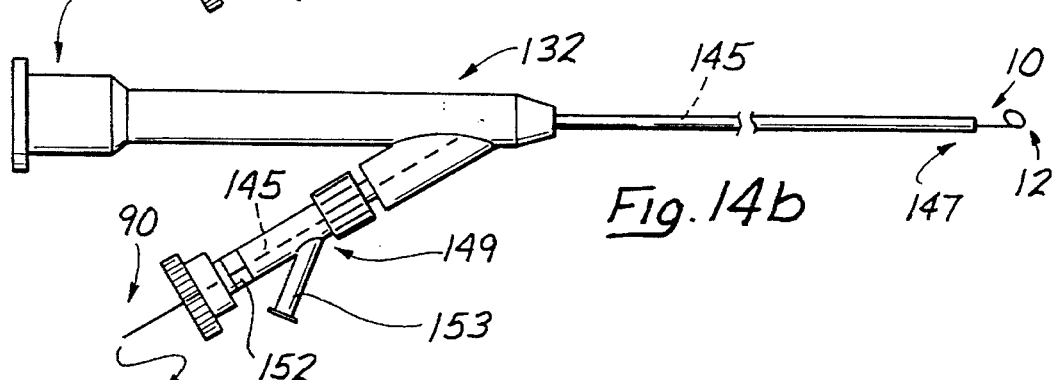
FIG. 14B illustrates a further assembly step where a pin vice is attached to the valvulotome.
Figure 15:
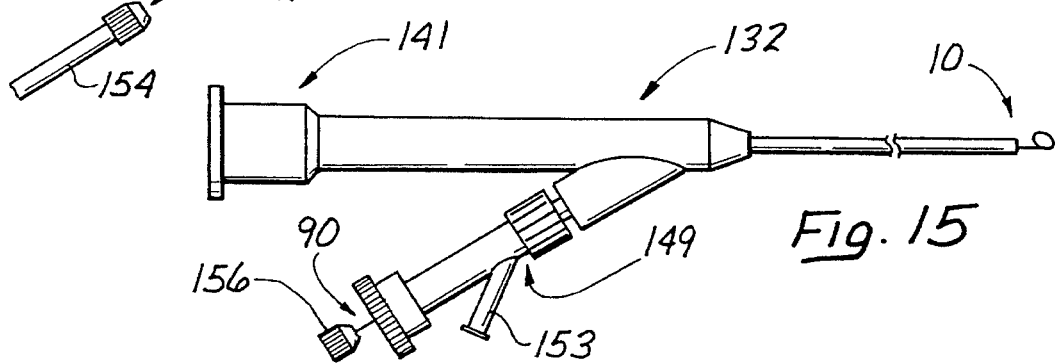

FIGS. 13–15 illustrate a preferred method for assembling the combination in FIG. 12. In FIG. 13A, the valvulotome 10 is illustrated with the elongate control member 14 extending between the proximal end 90 and distal end 92. The cutting head 12 is formed with the elongate section 101 integral with and extending distally of the control member 14 at the distal end 92. FIG. 13B illustrates the side view of the endoscope 132 with an eyepiece 141 at a proximal end 143 and a working channel 145 extending to a distal end 147.

In a preferred method, the proximal end 90 of the valvulotome 10 is back-loaded into the working channel 145 of the endoscope 132 at the distal end 147. This step is illustrated in FIG. 14A. In FIG. 14B, the proximal end 90 has been fully inserted into the working channel 145 and extends through a Y-fitting 149 attached to the endoscope 132 at the proximal end of the working channel 145. In a preferred embodiment, this Y-fitting 149 includes a compression seal 152 which is axially compressible to radially engage the control member 14. Where the control member 14 clears the compression seal 152, a pin vice 154 can be attached to the proximal end 90 where the vice 154 functions as a handle facilitating the axial and rotational movement of the control member 14 and cutting head 12.

In the resulting embodiment the cutting head 12 can be moved axially and rotationally within the working channel 145 by operation of the handle or vice 154. As noted, it may be desirable to fix the control member 14 axially within the working channel 145. This can help maintain the focal point 138 of the endoscope 132 on the cutting edge 114 of the cutting head 12. In the illustrated embodiment, this fixed axial relationship can be maintained by tightening the compression seal 152. Notably, there still remains the ability to rotate or torque the control member 14 within the seal 152 even when its axial movement is inhibited. The axial seal 152 of course functions as a seal so that various drugs can be injected through a side channel 153 into the working channel 145 to exit the endoscope 132 at its distal end 147 in proximity to the cutting head 12.

A further embodiment of the invention is illustrated in FIG. 15. This embodiment is similar to that discussed with reference to FIGS. 13 and 14 but the final assembly of the combination is accomplished by the manufacturer rather than the surgeon. As a result, the manufacturing process includes the back-loading of the valvulotome 10 into the endoscope 132 by the manufacturer. When the proximal end 90 of the control member 14 clears the Y-fitting 149, a torque knob 156 can be permanently molded onto the proximal end 90 of the endoscope 10. This completed assembly can then be sterilized and sold as a completed combination, no further assembly being required by the surgeon.

Although dimensions will vary for a particular desired size of the valvulotome 10, the following dimensions are characteristic of the best mode embodiment. In this particular case the valvulotome 10 is formed from stainless steel wire having a diameter of 0.014 inches. The radius of curvature R of the lateral region 105 is 0.035 inches while the radius of curvature r in the transition region 109 is 0.010 inches. The elongate section 101 and return section 103 are generally parallel and are diametrically tangential to the curve forming the lateral section 105. The length of the cutting head 12 is approximately 0.183 inches from the distal-most end of the lateral section 105 to the proximal-most point 112 in the transition 109.

The width of the cutting head 12 in this embodiment is equal to the diameter of the curve forming the lateral section 105. It follows that the length-to-width ratio of this embodiment is 2.0 which is preferred for the axial orientation desired for the cutting head 12 within the vein 16. Length-to-width ratios in a range 2 and 4 are generally preferred. In an embodiment wherein the cutting section 107 is straight, the length of the section 107 is generally determined by the angle α. In an embodiment including the weld 115, the angle α is preferably less than 90° but greater than 30°. In a preferred embodiment, the angle α is 55° and the length of the cutting section 107 is about 0.06 inches.

In spite of the specificity outlined for this particular embodiment, it must be appreciated that the invention can be otherwise embodied. For example, the valvulotome 10 could be formed from different materials although the material in the cutting section 107 must be capable of holding a sharp edge. The radii R and r can vary considerably although it is generally desirable that some curvature occur at the respective locations. In a particular embodiment, the sections 101 and 103 may have other than a parallel orientation although this configuration seems to be preferred in most cases. The angle α between the cutting region 107 and the return region 103 can also vary considerably and may even be variable in a particular embodiment such as that discussed with reference to FIG. 9.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A valvulotome for disrupting a valve in a vein extending upstream from a heart to an extremity of the body, the vein having a radius and a central axis, the valvulotome comprising:

an elongate control member having a distal end and a length sufficient to position the distal end downstream of the valve from an entry site upstream of the valve; wherein the elongate control member has an axis of elongation which extends along its length;

a cutting head coupled to the control member at the distal end of the control member, the cutting head having a length and a width;

an elongate section included in the cutting head and extending generally along the length of the cutting head;

a return section included in the cutting head and extending beside the elongate section generally along the length of the cutting head, the return section having a proximal end;

a cutting section included in the cutting head and extending between the elongate section and the proximal end of the return section at a particular acute angle to the axis of elongation of the control member; and portions of the cutting section forming a proximal facing cutting edge for engaging and cutting the valve to disrupt the valve of the vein.

2. The valvulotome recited in claim 1 further comprising:

a transition section coupling the return section to the proximal end of the cutting section and having a generally arcuate configuration, portions of the transition section defining an extension of the proximal facing cutting edge.

3. The valvulotome recited in claim 1 wherein the elongate section, the return section, and the cutting section are generally straight, and the return section is configured to extend generally parallel to the axis of the vein.

4. The valvulotome recited in claim 3 wherein:

the valvulotome further comprises a lateral section included in the cutting head and extending generally along the width of the cutting head to support the return section at a position laterally spaced from the elongate section;

the lateral section has an arcuate configuration and is disposed between the elongate section and the return section at the distal-most point of the cutting head.

5. The valvulotome recited in claim 4 wherein the transition section includes a proximal-most point of the cutting head.

6. The valvulotome recited in claim 5 wherein:

the cutting head is formed from a wire;

the wire in the lateral section is bent in the form of a first circle having a first radius;

the wire in the transition section is bent in the form of a second circle having a second radius; and the first radius is greater than the second radius.

7. The valvulotome recited in claim 6 wherein the cutting head is in the form of a blade.

8. The valvulotome recited in claim 7 further comprising:

portions of the blade defining a hole between the elongate section and the return section; and means coupled to the cutting head at the hole for pulling the cutting head upstream through the vein.

9. The valvulotome recited in claim 1 wherein the width of the cutting head is greater than the radius of the vein.

10. A valvulotome comprising:

an elongate control member having a proximal end and a distal end;

a cutting head coupled to the distal end of the control member and having a length, a width, a distal end and a proximal end;

an elongate section included in the cutting head and extending generally along the length of the cutting head;

a return section included in the cutting head and extending beside the elongate section generally along the length of the cutting head;

a lateral section extending between the elongate section and the return section at the distal end of the cutting head;

a cutting section included in the cutting head and extending between the return section and the elongate section;

a transition section extending between the return section and the cutting section at the proximal end of the cutting head; and portions of at least one of the transition section and the cutting section defining a proximally facing cutting edge of the valvulotome.

11. The valvulotome recited in claim 10 wherein the elongate section and the return section are separated by the width of the cutting head.

12. The valvulotome recited in claim 10 wherein the elongate section comprises an extension of the control member.

13. The valvulotome recited in claim 12 wherein the return section is generally parallel to the elongate section.

14. The valvulotome recited in claim 10 wherein the elongate section, the return section, and the cutting section are disposed generally in a single plane.

15. The valvulotome recited in claim 10 wherein the cutting section is disposed at a particular angle to the return section and the particular angle is less than 90°.

16. A valvulotome, comprising:

an elongate control member;

a cutting head having a distal end and a proximal end including a proximal most point, the cutting head being fixed to the control member and extending distally and laterally of the control member;

a return section of the cutting head disposed laterally of the control member and including a rounded surface disposed along an outer edge of the cutting head;

a cutting section disposed at the proximal end of the cutting head between the return section and the control member, the cutting section including a proximally facing cutting edge which extends distally with progressive positions from the return section to the control member;

a transition section disposed between the return section and the cutting section, the transition section including an extension of the rounded surface of the return section and extensions of each of the sharpened surfaces of the cutting section; and the proximal most point of the cutting head being disposed along the extension of the rounded surface in the transition section.

17. The valvulotome recited in claim 16 wherein the cutting section including a first surface and a second sharpened surface which converge to form the proximally facing cutting edge.

18. The valvulotome recited in claim 17 wherein the transition section includes a wedge defined by an intersection of the rounded surface and each of the sharpened surfaces; and the proximal most point of the cutting head is disposed in the wedge of the transition section.

19. A combination for disrupting a valve in a vein to facilitate the flow of blood to an extremity of the body, the combination comprising:

a valvulotome for cutting the valve;

an elongate control member included in the valvulotome;

a cutting head included in the valvulotome and coupled to the control member, the cutting head having a length extending between a proximal end of the cutting head and a distal end of the cutting head;

portions of the cutting head defining a cutting edge at the proximal end of the cutting head;

an endoscope sized and configured for insertion into the vein, the endoscope having a focal length; and means for coupling the endoscope to the distal end of the cutting head at a particular distance dependent on the focal length of the endoscope.

20. The combination recited in claim 19 wherein the coupling means includes a suture.

21. The combination recited in claim 19 wherein the particular distance orients the endoscope with its focal point disposed along the cutting edge of the cutting head.

22. A combination for disrupting a valve in a vein to facilitate the flow of blood to an extremity of a body, the combination comprising:

an elongate endoscope having an axis extending between an eyepiece at a proximal end of the endoscope and a focal point near a distal end of the endoscope;

a valvulotome extending from the distal end of the endoscope and having a distal end facing away from the endoscope and a proximal end, the valvulotome including an elongate section extending generally parallel to the axis of the endoscope,;

a return section extending along the elongate section, the return section having a proximal end, and a cutting section extending between the elongate section and the proximal end of the return section and disposed at an angle less than 90° to the axis of the endoscope, and means for maintaining the valvulotome in a fixed relationship with the endoscope with the focal point of the endoscope disposed relative to the cutting edge of the valvulotome.

23. A method for disrupting a valve in a vein disposed between a downstream end in proximity to the heart and an upstream end in proximity to an extremity of the body, comprising the steps of:

providing an elongate valvulotome having a cutting head with a proximal end, a distal end, and a sharpened cutting edge disposed at the proximal end;

providing an endoscope having a proximal end and a distal end, the endoscope having a focal point;

inserting the cutting head of the valvulotome into the vein through a first incision upstream of the valve;

moving the cutting head downstream through the valve;

exiting the cutting head from the vein through a second incision downstream of the valve;

coupling the distal end of the endoscope to the distal end of the cutting head;

pulling the cutting head and the endoscope into the vein through the second incision and upstream to the valve;

cutting the valve with further movement of the cutting head upstream in the vein; and during the cutting step viewing the cutting of the valve through the endoscope from a position downstream of the cutting head.

24. The method recited in claim 23 wherein the coupling step includes the step of orienting the endoscope relative to the cutting head with the focal point of the endoscope disposed generally along the cutting edge.

25. The method recited in claim 23 further comprising the steps of:

providing a hole in the cutting head of the valvulotome; and during the cutting step, suturing the endoscope to the hole in the cutting head of the valvulotome.

26. The method recited in claim 23 wherein the cutting step includes the step of engaging a downstream side of the valve with the cutting edge on the proximal end of the cutting head to cut the valve.

27. The method recited in claim 26 wherein the cutting head has a proximal-most point and the engaging step includes the step of initially contacting the downstream side of the valve with the cutting edge at the proximal-most point of the cutting head.

\* \* \* \* \*